United States Patent [19]

Price

[11] 4,029,553

[45] June 14, 1977

[54] PURIFICATION OF ACETIC ACID STREAMS BY DISTILLATION

[75] Inventor: Jerry L. Price, Texas City, Tex.

[73] Assignee: Monsanto Company, St. Louis, Mo.

[22] Filed: July 28, 1975

[21] Appl. No.: 599,506

[52] U.S. Cl. .................................. 203/94; 203/98; 260/941

[51] Int. Cl.² ..................... B01D 3/10; C07C 53/08

[58] Field of Search .............. 203/94, 98; 260/541, 260/532

[56] References Cited

UNITED STATES PATENTS

| 3,769,177 | 10/1973 | Eubanks | 203/98 |
| 3,772,156 | 11/1973 | Johnson | 203/33 |
| 3,772,380 | 11/1973 | Paulik | 260/541 |
| 3,791,935 | 2/1974 | Eubanks | 260/541 |

Primary Examiner—Hiram H. Bernstein
Attorney, Agent, or Firm—Elizabeth F. Sporar

[57] ABSTRACT

Acetic acid containing very minor amounts of iodine, either as I⁻, free iodine, or alkyl iodide, or all of these, is purified by fractionation in a single column with an acid product containing 20 parts or less of iodine per billion parts of acid (ppb) being withdrawn as a liquid sidedraw from said column. Generally, more than one column is required for obtaining an acid product of such extremely high purity. The process is particularly applicable for purification of acetic acid made by the carbonylation of methanol using a catalyst system formed on the mixing of a rhodium or iridium component and an iodine component notably hydrogen iodide or an alkyl iodide such as methyl iodide.

10 Claims, 2 Drawing Figures

PURIFICATION OF ACETIC ACID STREAMS BY DISTILLATION

BACKGROUND OF THE INVENTION

The present invention relates to the purification of carboxylic acid streams. More particularly, it relates to the purification of an acetic acid stream containing very minor amounts of iodine as an impurity.

A process has recently been developed for the preparation of carboxylic acids by the reaction of an alcohol or an ester, or ether and halide derivatives thereof, with carbon monoxide in contact with catalyst systems formed on mixing of a rhodium or iridium component and an iodine component in the presence of carbon monoxide. Hydrogen iodide or an alkyl iodide, notably methyl iodide, is usually employed as the iodine component in these catalyst systems. While the carboxylic acids produced by this process are generally of relatively high purity, they sometimes contain residual amounts of iodine either as ionic iodine, free iodine or as alkyl iodide, especially methyl iodide. Such contaminants render the acids unfit for certain uses. For example, the acetic acid containing them cannot be employed in certain processes in which the catalyst used is sensitive to the presence of even trace amounts of iodine. In some instances, in order to be useful as a raw material acetic acid must contain no more than 20 parts by weight of iodine or less billion parts by weight of acid(20 ppb) and preferably less than 10 ppb.

Suitably pure carboxylic acids, that is, carboxylic acids containing less than 20 ppb iodine, can be produced by fractionation techniques such as that described, for example, in Belgian Pat. No. 776,099 granted Oct. 22, 1971. This system involves introducing the acid stream containing the iodine contaminant into a first fractionation column, taking a fraction from the upper half of this column and introducing it into the upper half of a second fractionation column, removing a light overhead fraction containing primarily alkyl iodide from the second column and removing a product stream at or near the bottom of the second column, the product stream being virtually free of the iodine component. However, as distillation proceeds in such a system, there is a continuous generation of an iodine impurity. Frequent analysis of the feed material and the overhead product of the first fractionation column shows that the total iodine content of the overhead is consistently greater than that observed in the feed. This effect is believed to be attributable primarily to solvolysis or hydrolysis of metal iodides such as those of nickel, iron, chromium and molybdenum which are present in the system as corrosion products as well as to hydrolysis of any alkyl iodides which may also be present. Also, because of the precise control required to maintain the iodine at the exceedingly low levels required by product specifications, an upset in any part of the purification system caused, for example, by the temperature going out of control or by inadvertent admission of air into a column, rapidly affects the whole system, resulting in the specifications at any particular point in the system with respect to iodine content being exceeded by as much as 10 to 100 times. In such cases, too, free iodine can be produced which causes undesirable discoloration in the acid stream.

To overcome the difficulties of the process described above, fractionation can be effected in the presence of certain chemical agents in the manner described in U.S. Pat. No. 3,772,156. However, the advantages of a process for the purification of acetic acid in a single fractionation column whereby minor amounts of iodine or iodine-containing impurities can be removed to exceedingly low levels for consistent production of a product containing less than 20 ppb iodine while minimizing amounts of chemical agents used are immediately obvious. It is an object of the present invention to provide such a process which in addition to minimizing the need for added chemicals, results in reduced energy requirements and reduced capital investment since it is possible to eliminate altogether the product stripping column which is conventially employed in the purification schemes of the prior art.

SUMMARY OF THE INVENTION

This and other objects and advantages of the invention which will become obvious from the following description thereof are realized in the purification process which comprises introducing a stream of acetic acid containing minor amounts of iodine, either as $I^-$, free iodine or alkyl iodide, or all of these, into the intermediate section of a fractionation column, withdrawing any high-boiling impurities from the bottom of said column, withdrawing and condensing the overhead vapors from said column, withdrawing a minor portion of said condensate, generally an amount not exceeding 10% by weight thereof, returning the remainder of said condensate as liquid reflux to the top of said column, and withdrawing acetic acid containing 20 ppb or less of iodine as a liquid sidedraw from the upper one-fourth of said column. Generally, the liquid sidestream product is removed from the column at a level as close as possible to the liquid reflux level, i.e., from about two to about five trays from the top of the column. In the preferred embodiment of the invention, only a single fractionation column is required. However, the separation process of the invention can be used in conjunction with a second column, if desired, to provide ultra pure product with respect to iodine contamination (<5 ppb iodine) i.e., reducing iodine content still further, in which case, the liquid sidedraw product is introduced into the corresponding section of a stripping column where iodine concentration would be still further reduced by stripping iodine overhead and recovering pure acetic acid either as a vapor or a liquid or both from the bottom section of the stripping column.

DESCRIPTION OF THE PREFERRED EMBODIMENT

Figure 2:
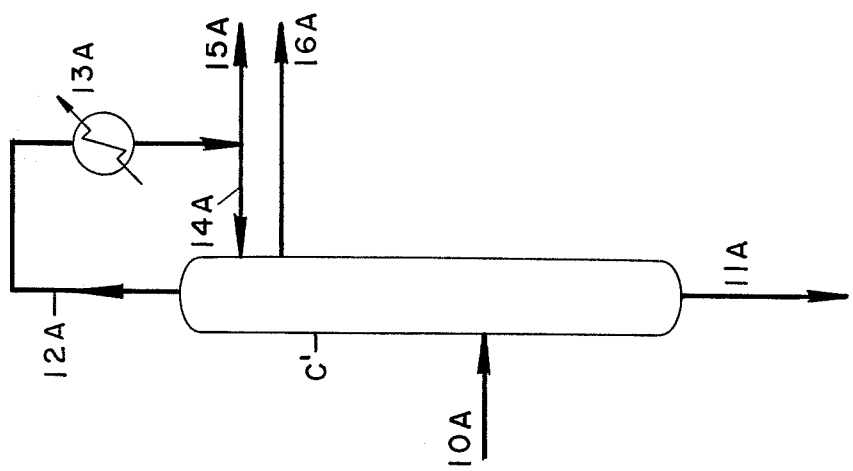
Figure 1:
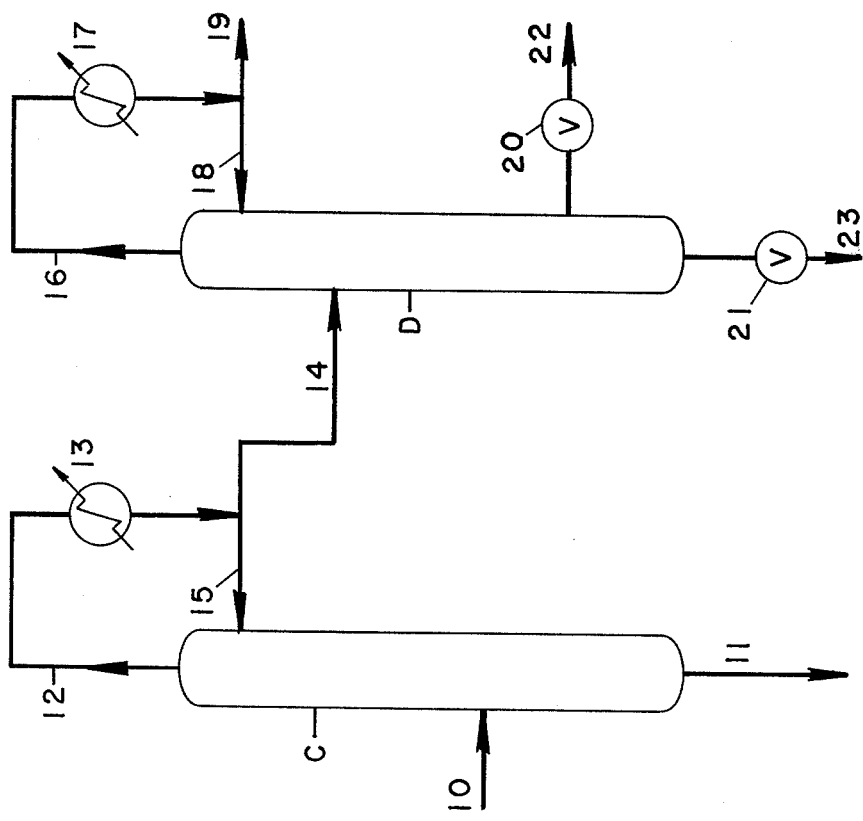

The process of the invention will be more clearly understood from the following description of a specific embodiment with reference to the attached FIGS. 1 and 2 wherein FIG. 1 is a diagrammatic flow diagram of the conventional method of fractionation, and FIG. 2 is a diagrammatic flow diagram of the preferred embodiment of the invention.

Reference is now made to FIG. 1 for the description of a purification process which represents the conventional operation. The acetic acid stream to be purified is introduced via line 10 into the intermediate section of fractionation column C and preferably at a point near the mid-point of column C. A heavy-ends waste product, generally constituting only a few percent of the total feed to column C is removed via line 11 and sent to waste disposal. This bottom product generally contains products and by-products boiling higher than acetic acid, other non-volatiles and the like. Vapors leaving column C via line 12 are condensed in the condenser 13, the condensed stream passing via line 14 to a second fractionation column D. As shown, provision can be made via line 15 to recycle part of the stream from condenser 13 back to column C to serve as reflux.

The stream entering D via line 14 is introduced above the mid-point of the column. Overhead vapors from D are removed via line 16 and condensed in condenser 17, a portion being sent back as reflux to column D via line 18 if desired and a portion of the total overhead being removed via line 19. The overhead material removed via line 19 can be either collected and disposed of or recycled to some point upstream of column C.

The product stream from column D is removed from the lower half of column D and this can be accomplished in several ways. With valves 20 and 21 open, the main product is removed via line 22 passing through valve 20. A small bleed stream coming via line 23 through valve 21 is then recycled to an intermediate point in column C. Alternatively, valve 20 can be closed and the entire product stream can be removed from column D through line 23 passing through valve 21. In either event, the net waste from the process is disposed of through line 11 coming from column C.

In FIG. 2 which represents the preferred embodiment of the present invention, only one column is employed which can be identical to column C in FIG. 1. The acetic acid stream to be purified is introduced via line 10A into the intermediate section of column C'. Impurities boiling higher than acetic acid are removed from the bottom of the column via line 11A and sent to waste disposal facilities. The vapors rising overhead from the column pass through line 12A and through condenser 13A where they are condensed. The major portion of the condensate is returned as liquid reflux to the column through line 14A while a portion of the condensate which is usually less than 10% by weight of the whole stream is removed via line 15A. The material removed can be collected and disposed of or recycled to some point upstream of column C'. A liquid stream of product acetic acid containing less than 20 ppb iodine is withdrawn through line 16A and passed to suitable storage facilities.

The invention is illustrated in the following examples which, however, are not to be considered as limiting it in any manner whatsoever. Unless otherwise specified, all parts recited are parts by weight.

EXAMPLE 1

Acetic acid prepared by the carbonylation of methanol in the presence of a catalytic system formed on mixing of a rhodium component and an iodine component in the presence of carbon monoxide was purified in a pilot plant purification system set up essentially like that shown in FIG. 1. The first column of stainless steel approximately 6 inches in diameter, was packed with 33 feet of ½-inch Intalox saddles and equipped with a thermosyphon shell and tube reboiler with 200 psi steam on the shell side, a shell and tube condenser with cooling tower water on the shell side and an overhead reflux tank and reflux pump. The feed tray was located above the second section of packing (approximately 21 feet down from the top of the column). A liquid sidedraw tray was located above the fourth section of packing (approximately 7 feet down from the top of the column). The second column was a 2-inch Oldershaw-type having about 30 plates equipped with a Thiele-type circulating glass reboiler with electrically heated sidearms and fittings for liquid removal and a thermowell, a liquid dividing stillhead, a glass reflux condenser and an overhead distillate cooler. A specially made draw-off joint was installed above the reboiler to withdraw product as vapor and condense it.

A stream of crude acetic acid (99 +percent) containing approximately 210 ppb $I^-$, 30 ppb MeI and 900 ppm propionic acid was introduced through line 10 into the first of the two distillation columns C at a rate of about 75 lb/hr. Distallation was conducted at substantially atmospheric pressure with the overhead temperature at 118° C and bottoms temperature slightly higher. The overhead vapors from the column were withdrawn through line 12, condensed in a water-cooled condenser 13, and a portion thereof (~10%) was introduced into the second distillation column D at about the 5th tray from the top, the remainder being by-passed to a collecting vessel because of column size limitations. The stream from the bottom of the first distillation column, approximately 1% of the feed to this column, containing propionic acid and other high-boiling impurities was removed via line 11 and sent to waste disposal facilities. A portion of the overhead condensate (56%) was returned to the top of the column as reflux by line 15.

Operating conditions of temperature and pressure in the second distillation column D were essentially the same as in the first column D. The overhead vapors from the second column constituting about 30 percent of the total feed to this column were removed through line 16 and passed through a condenser 17 with about 50% of the condensate being returned to the column D as reflux and the remainder withdrawn via line 19 and recycled to a point upstream of the purification unit. A liquid draw-off was removed from the bottom of the second distillation column through valve 21 and a tapwater exchanger and pumped to a receiver. A vapor stream was withdrawn from near the bottom of column D and condensed in a glass condenser at tap-water temperature. The liquid product from this condenser was then pumped to a product receiver.

The system as described was operated continuously over a period of several days while samples of the overhead from the first column C which was the feed to the second column D and the overhead and vapor products from the second column were taken periodically and analyzed for their $I^-$ and $I_2$ content determined as $I^-$, total inorganic iodide, and for methyl iodide. Results are presented in Table 1 below. These data show that to obtain acetic acid with an iodine content of 20 ppb or less, a two-column distillation system is required since the iodine content in the overhead stream from the first column is high but this material primarily goes overhead in the second column. In considering the data, it should be recognized that a complete balance of iodine, i.e., iodine in and iodine out of the system, cannot readily be calculated because of the dynamic equilibrium prevailing in the column wherein there is a continuous generation of an iodine impurity.

TABLE 1

| Day | Time | OH Col. C (ppb) $I^-$ | Mel | OH Col. D (ppb) $I^-$ | Mel | Bottoms Vapor Prod. (ppb) $I^-$ | Mel |
|---|---|---|---|---|---|---|---|
| 1 | 1600 | 132 | 17 | 1000 | 50 | 6 | 12.5 |
|  | 2300 | 210 | 12 | 2800 | 74 | 3 | 5 |

TABLE 1-continued

| Day | Time | OH Col. C (ppb) I⁻ | OH Col. C (ppb) MeI | OH Col. D (ppb) I⁻ | OH Col. D (ppb) MeI | Bottoms Vapor Prod. (ppb) I⁻ | Bottoms Vapor Prod. (ppb) MeI |
|---|---|---|---|---|---|---|---|
| 2 | 0700 | 310 | 24 | 1200 | 58 | 1 | 2 |
|   | 1600 | 385 | 26 | 1960 | 113 | 3 | 4 |
|   | 2300 | 120 | 16 | 800 | 66 | 2 | 6 |
| 3 | 0700 | 130 | 23 | 2700 | 80 | 1 | 15 |
|   | 1530 | 80 | 22 | 1100 | 76 | 1 | 7 |

EXAMPLE 2

The first of the columns described in Example 1 (Column C) was used alone to purify crude acetic acid of a constitution similar to that subjected to purification in Example 1. Conditions of temperature and pressure were essentially the same as in Example 1. The stream of acetic acid (99 +%) containing amounts of free iodine ($I_2$) ionizable iodine ($I^-$) and methyl iodide in the parts-per-billion range and propionic acid in the parts-per-million range was introduced into the column C' through line 10A at a rate of about 75 lb/hr. The overhead vapors were taken off through line 12A and were condensed with all but about 5% of the condensate being returned to the column as reflux via line 14A. The remaining condensate was withdrawn through line 15 and recycled to a point upstream of the purification train. A bottoms stream containing propionic acid (75 to 80,000 ppm) and other high boiling impurities was withdrawn at a rate of about 1% of the feed through line 11A and discarded. The balance of the column product was removed as a liquid sidedraw through line 16A at a rate of 70 lb/hr from the tray located above the fourth section of packing, a distance approximately 7 feet down from the top of the column, and collected in a drum. Two spot samples were taken of the sidedraw material, one of the overhead material and a fairly representative sample of the drum was also collected. These samples were analyzed for iodine and propionic acid content by gas chromatography techniques with results as follows:

| Time | Sample | I⁻ ppb | MeI ppb | HOPr ppb | Other |
|---|---|---|---|---|---|
| 1600 | Sidedraw | 43 | 1 | | |
| 2000 | " | 14 | 9 | 20 | |
| 2000 | Overhead | 74 | 63 | Trace | Water = 40 ppm |
| Representative Sample of Drum | | 9 | 10 | 34 | |

As is evident from the examples, iodine contamination in acetic acid can be reduced by distillation in a single column to exceedingly low concentrations so as to provide acid of such extremely high purity that it can be employed as a raw material essentially for all purposes. The invention is, of course, not to be considered as being limited to what is specifically set forth in the example. Any type distillation column, for instance, normally used for separation and purification can be employed for the purification and it can be either the packed- or plate-type or a combination of the packed-plate type. Generally, the column will be a plate-type column having from 45 to 80 and preferably 60 to 75 trays. In an especially preferred embodiment, sieve trays are employed although other type trays such as bubble cap and ballast may be used.

The temperature and pressures employed may vary considerably. Usual pressures for operation are those from approximately atmospheric to about 50 psig although subatmospheric pressures may be employed if desired as well as superatmospheric pressures well in excess of 100 psig. Preferably, however, in the purification of acetic acid, the distillation column is usually operated at a pressure within the range of 0 to 25 psig.

Temperature within the column will normally be between the boiling point of the acetic acid being purified at the pressure of the column and the temperature at which a satisfactory boil-up rate is achieved at such pressure. At the preferred pressures, the bottoms temperature generally will be within the range of from approximately the boiling point of the acid at the pressure employed to as high as 205° C and higher. Preferably, however, the bottoms temperature is maintained below 163° C.

While the point of introduction of the feed stream to the column can vary intermediate the ends of the column, the feed stream usually is introduced near the mid-point of the column and preferably into the lower half of the column.

The percentage of total feed removed as the overhead fraction from the column can vary over wide limits such as from 1–50% by weight. However, for practical and economic reasons, the amount withdrawn should not exceed 10% by weight and preferably should be from about 1% to about 5% by weight. The remainder of the overhead stream is returned to the column as liquid reflux.

In order to ensure that the product acetic acid stream contains the very minute quantities of iodine desired (20 ppb or less), the product is removed as a liquid sidedraw at a point in the upper quarter of the column. The liquid side-draw tray is located as close as possible to the tray on which the liquid reflux is introduced into the column. Generally, this tray is in the upper half of the top quarter of the column, i.e., at a point which is one-eighth of the distance down from the top of the column. In a 70-tray column, for example, the liquid sidedraw would be taken from a point between the first and the 18th tray and preferably from about the 2nd to the 5th tray from the top.

The bottoms stream generally comprises between about 0.5 and 2 percent by weight of the total feed to the column and preferably is from about 0.5 to about 0.8 percent by weight of the feed stream to the column.

What is claimed is:

1. A process for the removal of very minor amounts of iodine from acetic acid which consists of introducing acetic acid containing very minor amounts of propionic acid and other high-boiling impurities and iodine into the intermediate section of a fractionation column, withdrawing propionic acid and high-boiling impurities from the bottom of said column, withdrawing and condensing the overhead vapors from said column, withdrawing a minor portion of said condensate and returning the remainder of said condensate as liquid reflux to the top of said column and withdrawing an acetic acid product containing 20 ppb or less of iodine as a liquid sidedraw below the point of reflux entry in the upper one-fourth of said column.

2. The process of claim 1 wherein said acetic acid stream is introduced into the lower one-half of said fractionation column.

3. The process of claim 2 wherein said minor portion of said condensate constitutes from about 1 to about 50% of said total condensate.

4. The process of claim 3 wherein said minor portion of said condensate is less than about 10% of said total condensate.

5. The process of claim 3 wherein said minor portion of said condensate is from about 1 to about 5% of said total condensate.

6. The process of claim 5 wherein said acetic acid product is withdrawn from the upper one-eighth of said fractionation column.

7. The process of claim 4 wherein said fractionation column contains from about 45 to about 80 trays.

8. The process of claim 7 wherein said acetic acid product is withdrawn from about the second to the fifth tray from the top of said column.

9. The process of claim 8 wherein the temperature of said fractionation column is maintained between the boiling point of acetic acid to about 205° C.

10. The process of claim 9 wherein the pressure in said fractionation column is in the range from about 0 psig to 25 psig.

* * * * *